United States Patent [19]

Champion et al.

[11] Patent Number: 5,159,101

[45] Date of Patent: Oct. 27, 1992

[54] CYANOETHYLATION OF ALCOHOLS

[75] Inventors: Donald H. Champion, Pflugerville; George P. Speranza, Austin, both of Tex.

[73] Assignee: Texaco Chemical Company, White Plains, N.Y.

[21] Appl. No.: 833,199

[22] Filed: Feb. 10, 1992

Related U.S. Application Data

[63] Continuation-in-part of Ser. No. 539,946, Jun. 18, 1990, abandoned.

[51] Int. Cl.$^5$ ............................................. C07C 253/30
[52] U.S. Cl. .................................................... 558/450
[58] Field of Search .......................................... 558/450

[56] References Cited

U.S. PATENT DOCUMENTS 4,709,072  11/1987  Merger et al. ...................... 558/450
4,965,362  10/1990  Merger et al. ...................... 558/450 X
5,081,305   1/1992  Carr et al. .......................... 558/450 X

*Primary Examiner*—Joseph Paul Brust
*Attorney, Agent, or Firm*—Jack H. Park; Kenneth R. Priem; Cynthia L. Kendrick

[57] ABSTRACT

Disclosed is a process wherein cyanoethylation is accomplished by reacting a compound of the formula:

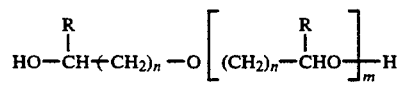

where R=H or CH$_3$, n=1 to 3 and m=0 to 50, and acrylonitrile over a heterogeneous catalyst comprising, potassium fluoride or cesium fluoride supported on an oxide of an element from the group consisting of Group IA, IIA or IIIA of the Periodic Table.

14 Claims, No Drawings

CYANOETHYLATION OF ALCOHOLS

This is a continuation-in-part of U.S. application Ser. No. 07/539,946, filed Jun. 18, 1990, now abandoned.

TECHNICAL FIELD OF THE INVENTION

The invention relates to cyanoethylation of alcohols. More particularly this invention relates to a novel catalyst for the cyanoethylation of compounds of the formula:

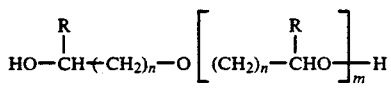

where R=H or CH$_3$, n=1 to 3 and m=0 to about 50. The method for cyanoethylation provides easier separation of the catalyst from the reaction mixture and provides bis(cyanoethyl)ethers which are lighter in color than products manufactured by conventional methods. The novel catalyst consists essentially of a fluoride-containing compound supported on an oxide of an alkali earth IA metal, an alkaline IIA element or an element of Group IIIA (CAS designation).

DESCRIPTION OF RELATED ART

Cyanoethylation reactions are well-known in the art as a convenient route for adding an active hydrogen across the double bond of acrylonitrile. Examples of chemical types that undergo cyanoethylation include hydroxyl compounds, thiols, nitrogen compounds, some carbon compounds, hydrogen chloride, hydrogen bromide, sodium bisulfite, arsines, boranes, germanes, phosphines, silanes and stannanes. The characteristic feature of compounds which can undergo this reaction is their possession of a labile hydrogen atom that, once removed, produces a nucleophilic group which attacks the most positive position in acrylonitrile.

The generally accepted mechanism for cyanoethylation is represented as follows where an alcohol is used as a reactant with acrylonitrile:

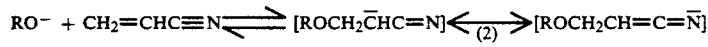

It is generally accepted that effective catalysts for cyanoethylation are strong bases, such as, for example, hydroxides, oxides, alkoxides, cyanides, hydrides, and amides of alkali metals. Under certain circumstances acids are effective. Solvents are often desirable to control the highly exothermic reaction. See "Cyanoethylation", Kirk-Othmer Encycl. Chem. Technol. 3rd Ed. 1979, Vol. 7, p. 370.

G. B. Patent No. 984,372 discloses that greater yields of cynaoethyl ethers are obtained using an excess of acrylonitrile. About 2 to 4 moles of acrylonitrile were used for each equivalent of OH, using catalysts such as sodium methoxide, potassium hydroxide and benzyltrimethylammonium hydroxide at a reaction temperature less than 15° C. in order to maximize yield.

In J. Org. Chem. 1962, 27, 1920 there is discussed the preparation of bis(cyanoethyl)ether by cyanoethylation of diols over anion exchange resins.

Nowhere in the art does it appear that a heterogeneous fluoride-containing catalyst has been employed for cyanoethylation of compounds of the formula:

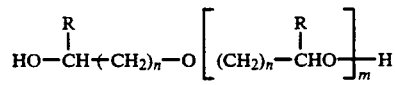

where R=H or CH$_3$, n=1 to 3 and m=0 to about 50. This would include, but not be limited to, for example, polytetrahydrofuran and polyalkylene glycols.

It would be very beneficial in the art if a supported cyanoethylation catalyst were developed which could be used continuously and could be easily separated from the reaction mixture. In cyanoethylation reactions conversions are typically high and, in order for such a catalyst to be beneficial, it would have to e demonstrated that nothing was lost in the way of conversion of the tetrahydrofuran or polyalkylene glycols and acrylonitrile.

SUMMARY OF THE INVENTION

In accordance with the present invention it has been surprisingly discovered that such benefits are observed by the use of a cyanoethylation catalyst comprising a fluoride-containing compound supported on an oxide of an alkali metal, an alkaline earth element or an element of Group IIIA, especially MgO, CaO, BaO or alumina.

The instant invention provides a method of obtaining high conversion levels of the glycols defined above and acrylinitrile in a method in which removal of the catalyst from the reaction mixture is facilitated by the fact that the catalyst is supported.

It was surprisingly discovered that, in addition to the above described benefits, which would constitute a substantial advantage, the reaction product unexpectedly displays the property of being lighter in color than any similar product produced by conventional methods.

DETAILED DESCRIPTION OF THE PREFERRED EMBODIMENT

According to the present invention there has been discovered a novel catalyst for cyanoethylation of glycols of the formula:

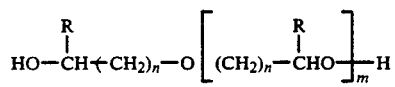

where R=H or CH$_3$, n=1 to 3 and m=0 to about 50, and acrylonitriles to cyanoethyl ethers which comprises a fluoride-containing compound supported on an oxide of an alkali metal, alkaline earth or an element of Group IIIA of the Periodic Table.

Further the invention comprises a method for reacting glycols of the above formula and acrylonitriles in the presence of the supported catalyst in a continuous fashion to produce high yields of cyanoethyl ethers, wherein the catalyst is as effective as catalysts of previous methods, but is more efficient in that, because of its nature, it can be easily separated from the reaction mixture.

The feedstock which can be reacted with acrylonitrile over the catalyst of the instant invention is of the chemical type including hydroxyl compounds such as, but not limited to water, alcohols, phenols and oximes. Other compounds which can be utilized include thiols, nitrogen compounds and some carbon compounds.

The Examples demonstrate, in particular, the reaction of polytetrahydrofuran and polyalkylene glycols plus acrylonitrile over cesium fluoride or potassium fluoride on an oxide support to produce, in the case of the examples, bis(cyanoethyl)ethers. Examples 1 through 25 demonstrate the cyanoethylation of polytetrahydrofuran and Examples 26 through 29 demonstrate the cyanoethylation of polyalkylene glycols having molecular weight from about less than 400 to at least 2000. The polyalkylene glycols include polyethylene glycols and polypropylene glycols. JEFFOX ® PEG is the tradename for polyethylene glycols having the formula:

where n is a number from about 1 to 50, manufactured by Texaco Chemical Col, having an average molecule weight of 200, 300, 400 or 600.

JEFFOX ® PPG is the tradename for polypropylene glycols of the formula:

where n is from about 1 to 50, manufactured by Texaco Chemical Co., having an average molecule weight of 400 to 2000. Use of dihydroxy compounds should also be considered an example, the reaction not being limited to these materials. Simple monoalcohols or more complex polyols behave analogously.

The general reaction can be represented by the following:

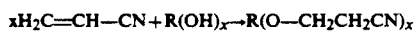

where
x = 1 or 2.

As stated, the novel catalyst of the instant invention comprises a fluoride-containing compound supported on an oxide of an alkali metal, alkaline earth element or Group IIIA element. Surprisingly, it does not appear that a broad range of fluoride-containing compounds can be used on the supported catalyst. Although the initial indication is that fluorides of Group IA of the Periodic Table should be useful, it was discovered that cesium fluoride and potassium fluoride are preferred while, as reported in Table I, with lithium fluoride and sodium fluoride no reaction was detected. In addition, aluminum fluoride on calcium oxide was found ineffective.

A wide variety of supports will work providing they are basic. The support can comprise an oxide of an alkali metal such as oxides of lithium, sodium, potassium, rubidium and cesium. Oxides of alkaline earth elements can also be used, such as, for example, barium calcium and strontium oxides. In addition, oxides of Group IIIA, including aluminum provide suitable supports. Specific examples include, but are not limited to basic alumina, barium oxide, calcium oxide and magnesium oxide.

As demonstrated in Examples 14-19 it was discovered that the fluoride-containing compounds alone were not as effective and the basic supports alone did not give conversion of the polyols used in the Examples. However, the basic supported catalysts gave improved conversions, even at higher temperatures than generally used in the art.

Generally the supported catalyst should comprise 10-50% by weight of the fluoride compound and preferably about 15-30% potassium fluoride or cesium fluoride on the described support.

The fluorine-containing compounds are impregnated on to the supports by simple dissolution of the fluoride in water, addition of the nonsoluble support and removal of water from the resulting mixture (see Bergbreiter, D. E. and LaLonde, J. J., *J. Org. Chem.*, 1987, 51 1601-1603). Materials consisting of 40% KF on alumina, 20% KF on silica and 50% KF on CELITE® are available from the Aldrich Chemical Co.

The cyanoethylation reaction is vigorous even at moderate temperatures and, in fact, high temperatures are to be avoided because the reaction has a tendency to reverse at high temperatures. Low temperatures are preferred. The reaction temperature can be from about 0°-100° C. and is preferably about 0°-50° C. The most preferred temperature is near or below room temperature.

Mild pressures are sufficient to effect the reaction. In fact, pressures from atmospheric to 150 psig are recommended. Most of the examples demonstrate the use of atmospheric pressure.

The time required to obtain high conversion levels may vary but generally is within a range of about 10 minutes to 2 hours and more typically was from about 15 minutes to 40 minutes.

A solvent was not required to carry out the reaction. A solvent may be desirable as a diluent to control the exotherm of reaction or to dissolve solid reactants which would otherwise require higher temperatures for the reactant to be in the liquid phase. Suitable solvents for cyanoethylation include inert hydrocarbons such as benzene, ethers such as dioxane, pyridine and acetonitrile tertiary butyl alcohol can also be used although it may itself become cyanoethylated above about 60° C.

The reaction may be carried out in a fixed bed continuous flow reactor.

The reaction was complete shortly after addition of the acrylonitrile in the useful examples. For less effective catalysts, such as cesium fluoride alone, prolonged heating may give higher conversions. A temperature rise of the reaction medium is observed in the cases where high conversion is obtained. In each case the hydroxyl number of the product mixture was determined and used as a measure of unreacted hydroxyl groups. The hydroxyl number of the reactant polytetrahydrofuran was in all cases 169. The lower the hydroxyl number in the product, the more complete a conversion was indicated.

An unexpected advantage is that the color of the product cyanoethyl ether is lighter than any produced by conventional methods. The product in most cases consisted of a yellow or slightly colored product. These products are more desirable than the darker cyanoethyl ethers produced by similar processes in the art.

The present invention will be further illustrated by the following examples which are only for the purpose of illustration and are not to be regarded as limiting the invention in any way.

EXAMPLE 1

To a 250 ml flask equipped with a magnetic stirrer, thermometer, nitrogen inlet and pressure equalized addition funnel were charged 100 g (0.301 eq) polytetrahydrofuran, hydroxyl number 169, and 4.0 g 20% potassium fluoride on basic alumina. Acrylonitrile (16.1 g, 0.303 mol) was added to the stirred mixture dropwise and an exothermic reaction ensured. External cooling was used to keep the temperature between 33°-40° C. After stirring an additional 2 hours at 24°-37° C., 1.0 g acetic acid was added to the mixture. It was then heated to 70° C. and filtered to give a slightly colored yellow liquid with OH number 30 (corrected for acid content).

EXAMPLES 2-13

The reaction described in Example 1 was repreated several times, the difference being the use of other supported fluoride catalysts. Except for cesium and potassium fluorides, no reaction was detected. It was also apparent that the support material is required to be basic. In cases where no exotherm was observed the addition funnel was replaced by a reflux condenser and the reaction mixture was heated for the indicated time. Table I summarizes the results.

Some of the products from the above reactions were analyzed for cation concentrations:

| Example | |
|---|---|
| 2 | 12 ppm K |
| 3 | 12 ppm K, <1 ppm Ba |
| 4 | 7.1 ppm K, 1.8 ppm Ca |
| 5 | 1.3 ppm K, <1 ppm Mg |
| 9 | 210 ppm Cs |

EXAMPLES 14-19

Cyanoethylation of polytetrahydrofuran, OH number 169, was attempted by the method of Example 1 using cesium fluoride and potassium fluoride. Little or no reaction resulted. These results show the basic supported catalysts give a higher conversion even at lower temperatures. Other experiments using the basic supports alone gave no conversion of the polyol. Table II summarizes the results.

TABLE II

Cyanoethylation of Polytetrahydrofuran OH Number 169 over Various Catalysts

| Ex. | Catalyst | Mass (g) | Addition (C) | Addition (h) | Stirring (C) | Stirring (h) | Product OH # | Product Color |
|---|---|---|---|---|---|---|---|---|
| 14 | CsF | 2.28 | 27-25 | 0.2 | 70 | 2.1 | 94 | slight |
| 15 | Anhydrous KF | 0.88 | 23 | 0.2 | 70 ca. | 3.0 | 164 | slight |
| 16 | spray dried KF | 0.88 | 28-29 | 0.1 | 70 ca. | 3.7 | 164 | slight |
| 17 | KF and 18-crown-6 | 0.88 4.0 | 32-31 | 0.1 | 70 ca. | 2.8 | 57 | light yellow |
| 18 | barium oxide | 2.3 | 27 | 0.2 | 70 | 2.0 | 163 | slight |
| 19 | basic alumina | 4.0 | 27-26 | 0.1 | | 3.0 | 167 | slight |

EXAMPLE 20

A mixture of 100 g polytetrahydrofuran, OH number 169 and 0.85 g 95% sodium methoxide was stirred at 45° C. to dissolve the catalyst. The addition of 16.1 g acrylonitrile was carried out at such a rate as to maintain the temperature of the reacting mixture between 29° and 40° C. This required 40 minutes. Subsequently, the mixture was stirred an additional 2 hours as it cooled to 26° C. After the addition of 1.0 g acetic acid, the brown product was analyzed and found to have a hydroxyl number of 19.

EXAMPLE 21

To 100 g polytetrahydrofuran, OH number 169, in the apparatus described in Example 1 was added 0.45 g

TABLE 1

Cyanoethylation of Polytetrahydrofuran OH Number 169 Over Various Fluoride Catalysts

| Ex. | Catalyst | Wt % F | Mass (g) | Addition (CO) | Addition (h) | Stirring (C) | Stirring (h) | Product OH # | Product Color |
|---|---|---|---|---|---|---|---|---|---|
| 1 | KF on basic alumina | 5.6 | 4.0 | 35-40 | 0.2 | 37-24 | 2.0 | 30 | slight |
| 2 | KF on basic alumina[a] | 13 | 4.0 | 32-41 | 0.2 | 41-23 | 2.0 | 7 | pale yellow |
| 3 | KF on BaO | 5.6 | 4.0 | 35-40 | 0.3 | 39-25 | 2.0 | 10 | 10 lt yellow |
| 4 | KF on CaO | 5.6 | 4.0 | 25-26 | 0.1 | 26-40 | 2.0 | 11 | 11 pale yellow |
| 5 | KF on MgO | 5.6 | 4.0 | 26-47 | 0.3 | 36-25 | 2.0 | 12 | 12 pale yellow |
| 6 | KF on Silica gel[a] | 5.6 | 4.0 | 25-24 | 0.2 | 70 | 3.1 | 176 | slight |
| 7 | KF-Celite @[a] | 16 | 4.0 | 32-29 | 0.2 | 70 | 3.4 | 153 | slight |
| 8 | CsF on basic alumina | 4.4 | 5.1 | 32-42 | 0.3 | 40-26 | 2.0 | 15 | yellow-or |
| 9 | CsF on basic alumina | 4.4 | 5.1 | 26-38 | 0.3 | 31-29 | 0.1 | 12 | yellow |
| 10 | CsF on calcium fluoride | | 5.1 | 26 | 0.2 ca. | 70 | 3.0 | 74 | pale yellow |
| 11 | LiF on basic alumina | 5.6 | 4.0 | 32-28 | 0.2 ca. | 70 | 3.0 | 174 | slight |
| 12 | NaF on basic alumina | 5.6 | 4.0 | 28-27 | 0.1 ca. | 70 | 2.8 | 167 | slight |
| 13 | aluminum fluoride on calcium oxide | 5.6 | 4.0 | 28 | 0.1 ca. | 70 | 3.0 | 175 | slight |

[a]Available from Alrich sodium hydride, 80% dispersion in mineral oil, at 40° C. The mixture was stirred for 40 minutes as gas evolved. Then 16.1 g acrylonitrile was added at such a rate as to maintain the reaction temperature between 25° and 41° C. without external cooling. After the 47 minutes required for the acrylonitrile addition, the mixture was further stirred for 2 hours as it cooled to 25° C. Acetic acid (1.0 g) was added to neutralize the mixture. The product was obtained as a yellow-orange liquid and found to have an OH number of 21.

EXAMPLE 22

To the apparatus described in Example 1 was charged 100 g polytetrahydrofuran, OH number 169, and 1.00 g 85% potassium hydroxide. The mixture was heated to about 80° C. for 15 minutes as the catalyst dissolved. Acrylonitrile, 16.1 g, was then added with external cooling at 28°-31° C. over 16 minutes. The mixture was further stirred at 23°-28° C. for 2 hours. After addition of 1.0 g acetic acid the resulting hazy, dark yellow product was found to have an OH number of 12 (corrected for acid).

EXAMPLE 23

The reaction of Example 1 was repeated using a larger amount (24.0 g, 0.452 mol) of acrylonitrile. No external cooling was used, the temperature being maintained by controlling the addition rate of the acrylonitrile. During the 30 minutes required for the addition the temperature of the reaction mixture was 24°-37° C. Subsequent stirring was done for 2 hours as the mixture cooled to 24° C. After the addition of 1.0 g acetic acid the mixture was heated before filtering to give a slightly colored product with OH number 20 (corrected for acid content).

EXAMPLE 24

The cyanoethylation of polytetrahydrofuran, OH number 169, was repeated by addition of 36.0 g (0.678 mol) acrylonitrile with cooling to a mixture of 150 g (0.452 eq) of the polyol and 6.0 g 40% potassium fluoride on alumina at 28°-47° C. After stirring for 2 hours at 26°-34° C., the product mixture was filtered and stripped at about 60° C. under high vacuum to give a yellow liquid. NMR analysis of the product showed a 99% conversion and the potassium content was found to be 15 ppm.

EXAMPLE 25

Cyanoethylation of Polytetrahydrofuran MW 2000. To 150 g (77.2 mmol) TERATHANE®2000 (hydroxyl number 57.78) and 6.0 g 40% KF/alumina with stirring under nitrogen was added 12.3 g (227 mmol) acrylonitrile at 45°-47° C. over 6 minutes. The mixture was stirred for 2 hours at 45°-47° C. Filtration of the product was difficult and was done overnight under a heat lamp. The filtrate was stripped under high vacuum at about 60° C. to give a thick orange liquid: OH number 6.1, 60 ppm potassium.

EXAMPLE 26

Cyanoethylation of PEG-600. The previous procedure was followed with 150 g (260 mmol) PEG-600 (3.460 meq/g OH), 6.0 g 40% KF/alumina and 41.3 g (779 mmol) acrylonitrile. Addition of the acrylonitrile was done with cooling at 30°-46° C. over 24 minutes. The mixture was subsequently stirred for 2 hours at it cooled to 24° C. It was then heated to about 40° C.,
filtered and vacuum stripped at about 60° C. for 1 hour to give an orange liquid: OH number 12, 37 ppm K.

EXAMPLE 27

Cyanoethylation of PEG-2000. The procedure for cyanoethylation of polytetrahydrofuran MW 2000 was followed with 150 g (75 mmol) PEG-2000, 6.0 g 40% KF/alumina and 11.9 g (224 mmol) acrylonitrile. Addition of the acrylonitrile was done at 55°-64° C. over 9 minutes. The mixture was subsequently stirred for 2 hours at 47°-57° C. It was then dissolved in glyme, filtered and vacuum stripped at 80°-90° C. for 2 hours after removing most of the solvent to give a brown solid: OH number 28, 1900 ppm K.

EXAMPLE 28

Cyanoethylation of PPG-400. The procedure for cyanoethylation of polytetrahydrofuran MW 2000 was followed with 150 g (0.349 mol) PPG-400, 6.0 g 40% KF/alumina and 55.5 g (1.05 mol) acrylonitrile. Addition of the acrylonitrile was done with cooling at 25°-38° C. over 28 minutes. The mixture was subsequently stirred for 2 hours as it cooled to 24° C. and then filtered with difficulty due to some gelatinous material present. The filtrate was vacuum stripped at about 70° C. for 1 hour to give an orange-brown product: OH number 31, 430 ppm K.

EXAMPLE 29

Cyanoethylation of PPG-2000. The procedure for cyanoethylation of polytetrahydrofuran MW 2000 was followed with 150 g (75 mmol) PPG-2000, 6.0 g 40% KF/alumina and 11.9 g (224 mmol) acrylonitrile. Addition of the acrylonitrile was done at 22°-24° C. over 7 minutes. The mixture was subsequently stirred for 2 hours at 24°-29° C. and treated with glyme. Filtration was difficult. A portion of the filtrate was vacuum stripped at about 70°-80° C. over 3 hours and refiltered to give an orange liquid: OH number 14, 130 ppm K.

What is claimed is:

1. A method for producing cyanoethyl ethers which comprises reacting an alcohol of the formula:

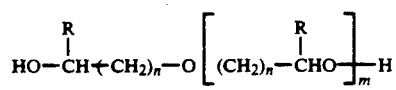

where R=H or CH$_3$, n=1 to 3 and m=0 to about 50 with acrylonitrile in the presence of a heterogeneous catalyst consisting essentially of a fluoride-containing compound from the group consisting of cesium fluoride and potassium fluoride supported on an oxide of a metal from the group consisting of IA, IIA or IIIA of the Periodic Table at a temperature in the range of 0°-100° C. and a pressure of from atmospheric to about 150 psig.

2. The method of claim 1 wherein the alcohol

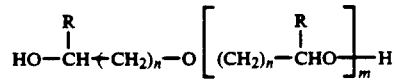

is selected from the group consisting of polytetrahydrofuran and polyalkylene glycols.

3. The method of claim 2 wherein the alcohol compound is polytetrahydrofuran.

4. The method of claim 2 wherein the polyalkylene glycol is selected from the group consisting of polyethylene glycols and polypropylene glycols.

5. The method of claim 4 wherein the polyethylene glycol has the formula:

where n is from about 1 to 50.

6. The method of claim 5 wherein the polyethylene glycols have molecular weights from about 200 to 600.

7. The method of claim 4 wherein the polypropylene glycol has the formula:

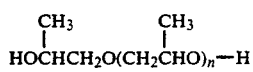

where n is from about 1 to 50.

8. The method of claim 7 wherein the polypropylene glycol has a molecular weight from about 400 to 2000.

9. The method of claim 1 wherein the oxide is selected from the elements of Group IA.

10. The method of claim 1 wherein the oxide of an element of Group IIA is selected from the group consisting of magnesium oxide, calcium oxide or barium oxide.

11. The method of claim 1 wherein the oxide of an element of Group IIIA is alumina.

12. The method of claim 1 wherein the temperature is in the range of 0°–100° C.

13. The method of claim 1 wherein the pressure is from atmospheric to about 150 psig.

14. The method of claim 1 wherein the heterogeneous catalyst allows separation of the product without distillation.

* * * * *